(12) United States Patent
Kankan et al.

(10) Patent No.: US 7,951,837 B2
(45) Date of Patent: May 31, 2011

(54) CRYSTALLINE FORMS OF DULOXETINE FREE BASE

(75) Inventors: Rajendra Narayanrao Kankan, Mumbai (IN); Dharmaraj Ramachandra Rao, Mumbai (IN); Srinivas Laxminarayan Pathi, Bangalore (IN); Revikumar Puppala, Bangalore (IN)

(73) Assignee: Cipla Limited, Mumbai (IN)

( * ) Notice: Subject to any disclaimer, the term of this patent is extended or adjusted under 35 U.S.C. 154(b) by 681 days.

(21) Appl. No.: 11/568,784

(22) PCT Filed: May 11, 2005

(86) PCT No.: PCT/GB2005/001825
§ 371 (c)(1),
(2), (4) Date: Jan. 11, 2007

(87) PCT Pub. No.: WO2005/108386
PCT Pub. Date: Nov. 17, 2005

(65) Prior Publication Data
US 2007/0167513 A1    Jul. 19, 2007

(30) Foreign Application Priority Data

May 11, 2004 (GB) .................................. 0410470.9

(51) Int. Cl.
*A01N 43/10* (2006.01)
*A61K 31/10* (2006.01)
*C07D 333/16* (2006.01)

(52) U.S. Cl. .......................................... 514/438; 549/75
(58) Field of Classification Search ................... 514/438
See application file for complete search history.

(56) References Cited

U.S. PATENT DOCUMENTS

| 4,956,388 A | 9/1990 | Robertson et al. |
| 5,023,269 A | 6/1991 | Robertson et al. |
| 5,491,243 A | 2/1996 | Berglund |

OTHER PUBLICATIONS

Guillory; "Generation of Polymorphs, Hydrates, Solvates, and Amorphous Solids"; 1999; in "Polymorphism in Pharmaceutical Solids"; Brittain, Ed.; Marcel Dekker, New York; pp. 183-202.*
Deeter, Jack, et al., "Asymmetric Synthesis and Absolute Stereochemistry of LY248686," Tetrahedron Letters, vol. 31, No. 49, 1990, Pergamon Press plc, Great Britain, pp. 7101-7104.
Sorbera, L.A., et al., "Duloxetine Oxalate: Treatment of Stress Urinary Incontinence Antidepressant Norepinephrine Reuptake Inhibitor 5-HT Reuptake Inhibitor," Drugs of the Future, vol. 25, No. 9, 2000, Prous Science, Barcelona, Spain, pp. 907-916, XP009034832.
Foreign communication from a related counterpart application—International Search Report, PCT/GB2005/001825, Aug. 18, 2005, 4 pages.
Foreign communication from a related counterpart application—International Preliminary Report on Patentability, PCT/GB2005/001825, Aug. 16, 2006, 7 pages.

* cited by examiner

*Primary Examiner* — Timothy Thomas
(74) *Attorney, Agent, or Firm* — Conley Rose, P.C.; Rodney B. Carroll

(57) ABSTRACT

The present invention is concerned with duloxetine free base in crystalline form, and also novel polymorphic forms thereof.

6 Claims, 3 Drawing Sheets

CRYSTALLINE FORMS OF DULOXETINE FREE BASE

CROSS-REFERENCE TO RELATED APPLICATIONS

This application is a filing under 35 U.S.C. 371 of International Application No. PCT/GB2005/001825 filed May 11, 2005, entitled "Crystalline Forms of Duloxetine Free Base," claiming priority of Great Britain Patent Application No. GB 0410470.9 filed May 11, 2004, which applications are incorporated by reference herein in their entirety.

FIELD OF THE INVENTION

The present invention is concerned with duloxetine free base in crystalline form, and also novel polymorphic forms thereof.

BACKGROUND OF THE INVENTION

Duloxetine, N-methyl-3-(1-naphthalenyloxy)-3-(2-thienyl)propanamine, is a dual serotonin and norepinephrine reuptake inhibitor. (+)Duloxetine has particular therapeutic utility as an anti-depressant.

Duloxetine, and the preparation thereof, is described in U.S. Pat. Nos. 5,023,269 and 4,956,388, and also Tetrahedron Letters, 31, (49), 7101-04, 1990. Seven different routes of synthesis have also been reported in Drugs of the Future 2000, 25(9) 907-916. These syntheses have involved either a resolution of a key intermediate or a stereospecific reduction of a keto group to the alcohol.

Isolation of duloxetine free base in crystalline form has not, however, been achieved by any of the processes described in the reported literature and patents.

SUMMARY OF THE INVENTION

There is now provided by the present invention, however, duloxetine free base in crystalline form.

The present invention further provides processes of preparing three different polymorphic forms of duloxetine, herein designated Forms A, B and C respectively, and these three polymorphic forms represent further embodiments of the present invention. As used herein, the term "duloxetine" preferably designates (+) duloxetine.

DETAILED DESCRIPTION OF THE INVENTION

According to the present invention, there is provided crystalline duloxetine free base, Form A, having an X-ray diffraction pattern, or substantially the same X-ray diffraction pattern, as shown in FIG. 1. More particularly, crystalline duloxetine free base Form A according to the present invention can be characterised as having an X-ray diffraction pattern with characteristic peaks (2θ): 9.70, 10.88, 13.03, 15.61, 19.19, 19.55, 19.88, 21.94, 22.16, 26.95 and 27.76°.

Further characterising data for crystalline duloxetine free base Form A according to the present invention as obtained by X-ray diffraction is shown in following table 1.

TABLE 1

| Peak No. | 2θ (deg) | FWHM (deg) | d (A) | Intensity (Counts) | I/I$_0$ |
| --- | --- | --- | --- | --- | --- |
| 1 | 9.700 | 0.212 | 9.1103 | 1107 | 27 |
| 2 | 10.880 | 0.188 | 8.1248 | 1372 | 34 |
| 3 | 12.050 | 0.165 | 7.3384 | 643 | 16 |
| 4 | 12.290 | 0.188 | 7.1956 | 721 | 18 |

TABLE 1-continued

| Peak No. | 2θ (deg) | FWHM (deg) | d (A) | Intensity (Counts) | I/I$_0$ |
| --- | --- | --- | --- | --- | --- |
| 5 | 13.030 | 0.294 | 6.7886 | 1548 | 38 |
| 6 | 13.910 | 0.129 | 6.3610 | 431 | 11 |
| 7 | 15.610 | 0.235 | 5.6719 | 2432 | 59 |
| 8 | 17.300 | 0.188 | 5.1214 | 652 | 16 |
| 9 | 17.770 | 0.318 | 4.9870 | 443 | 11 |
| 10 | 18.410 | 0.118 | 4.8151 | 599 | 15 |
| 11 | 19.030 | 0.153 | 4.6596 | 2632 | 64 |
| 12 | 19.190 | 0.235 | 4.6211 | 3098 | 75 |
| 13 | 19.550 | 0.176 | 4.5368 | 2429 | 59 |
| 14 | 19.880 | 0.235 | 4.4622 | 4143 | 100 |
| 15 | 20.170 | 0.165 | 4.3987 | 1332 | 33 |
| 16 | 20.910 | 0.271 | 4.2447 | 1119 | 27 |
| 17 | 21.200 | 0.200 | 4.1873 | 1127 | 28 |
| 18 | 21.940 | 0.271 | 4.0477 | 3684 | 89 |
| 19 | 22.160 | 0.200 | 4.0080 | 3494 | 85 |
| 20 | 22.730 | 0.106 | 3.9088 | 584 | 15 |
| 21 | 23.290 | 0.165 | 3.8160 | 713 | 18 |
| 22 | 23.420 | 0.129 | 3.7951 | 673 | 17 |
| 23 | 23.660 | 0.165 | 3.7572 | 718 | 18 |
| 24 | 24.350 | 0.235 | 3.6523 | 2351 | 57 |
| 25 | 24.810 | 0.224 | 3.5856 | 969 | 24 |
| 26 | 25.280 | 0.129 | 3.5200 | 950 | 23 |
| 27 | 25.460 | 0.188 | 3.4955 | 1042 | 26 |
| 28 | 26.070 | 0.106 | 3.4151 | 533 | 13 |
| 29 | 26.950 | 0.247 | 3.3055 | 1527 | 37 |
| 30 | 27.360 | 0.188 | 3.2569 | 1078 | 27 |
| 31 | 27.760 | 0.247 | 3.2109 | 1653 | 40 |
| 32 | 28.700 | 0.118 | 3.1078 | 638 | 16 |
| 33 | 29.460 | 0.318 | 3.0293 | 916 | 23 |
| 34 | 29.930 | 0.365 | 2.9828 | 1118 | 27 |
| 35 | 30.970 | 0.106 | 2.8850 | 763 | 19 |
| 36 | 31.130 | 0.188 | 2.8705 | 769 | 19 |
| 37 | 31.590 | 0.294 | 2.8298 | 1038 | 26 |
| 38 | 33.170 | 0.129 | 2.6985 | 575 | 14 |
| 39 | 33.520 | 0.106 | 2.6711 | 646 | 16 |
| 40 | 33.700 | 0.176 | 2.6573 | 668 | 17 |
| 41 | 33.940 | 0.118 | 2.6390 | 626 | 16 |
| 42 | 34.860 | 0.306 | 2.5715 | 685 | 17 |
| 43 | 36.370 | 0.118 | 2.4681 | 816 | 20 |
| 44 | 36.740 | 0.271 | 2.4441 | 1052 | 26 |
| 45 | 37.150 | 0.118 | 2.4180 | 954 | 24 |
| 46 | 37.330 | 0.118 | 2.4068 | 953 | 23 |
| 47 | 39.710 | 0.165 | 2.2679 | 806 | 20 |
| 48 | 40.090 | 0.176 | 2.2472 | 738 | 18 |
| 49 | 40.700 | 0.118 | 2.2149 | 658 | 16 |
| 50 | 41.050 | 0.153 | 2.1969 | 766 | 19 |
| 51 | 41.610 | 0.106 | 2.1686 | 883 | 22 |
| 52 | 41.690 | 0.141 | 2.1646 | 962 | 24 |
| 53 | 42.290 | 0.118 | 2.1353 | 770 | 19 |
| 54 | 42.420 | 0.129 | 2.1290 | 818 | 20 |
| 55 | 42.720 | 0.165 | 2.1148 | 692 | 17 |

According to the present invention, there is provided crystalline duloxetine free base, Form B, having an X-ray diffraction pattern, or substantially the same X-ray diffraction pattern, as shown in FIG. 2. More particularly, crystalline duloxetine free base Form B according to the present invention can be characterised as having an X-ray diffraction pattern with characteristic peaks (2θ): 4.98, 9.96, 11.18, 12.58, 15.32, 18.98, 20.04, 20.62, 22.32, 22.44, 27.28 and 30.30°.

Further characterising data for crystalline duloxetine free base Form B according to the present invention as obtained by X-ray diffraction is shown in following table 2.

TABLE 2

| Peak No. | 2θ (deg) | FWHM (deg) | d (A) | Intensity (Counts) | I/I$_0$ |
| --- | --- | --- | --- | --- | --- |
| 1 | 4.980 | 0.188 | 17.7294 | 915 | 17 |
| 2 | 9.960 | 0.212 | 8.8731 | 1269 | 23 |
| 3 | 11.180 | 0.235 | 7.9074 | 2278 | 41 |
| 4 | 11.580 | 0.212 | 7.6352 | 749 | 14 |

TABLE 2-continued

| Peak No. | 2θ (deg) | FWHM (deg) | d (A) | Intensity (Counts) | I/I₀ |
|---|---|---|---|---|---|
| 5 | 12.580 | 0.259 | 7.0304 | 1131 | 21 |
| 6 | 14.580 | 0.259 | 6.0702 | 576 | 11 |
| 7 | 15.320 | 0.282 | 5.7786 | 1767 | 32 |
| 8 | 17.860 | 0.118 | 4.9621 | 640 | 12 |
| 9 | 17.980 | 0.141 | 4.9293 | 690 | 13 |
| 10 | 18.980 | 0.353 | 4.6717 | 3036 | 55 |
| 11 | 20.040 | 0.235 | 4.4270 | 5583 | 100 |
| 12 | 20.620 | 0.282 | 4.3037 | 1716 | 31 |
| 13 | 21.000 | 0.306 | 4.2267 | 1383 | 25 |
| 14 | 22.320 | 0.306 | 3.9796 | 4190 | 76 |
| 15 | 22.440 | 0.141 | 3.9586 | 3576 | 65 |
| 16 | 23.220 | 0.141 | 3.8274 | 1435 | 26 |
| 17 | 23.340 | 0.188 | 3.8080 | 1498 | 27 |
| 18 | 23.840 | 0.259 | 3.7292 | 1382 | 25 |
| 19 | 24.560 | 0.118 | 3.6215 | 726 | 13 |
| 20 | 25.000 | 0.165 | 3.5588 | 1010 | 19 |
| 21 | 25.160 | 0.400 | 3.5365 | 1089 | 20 |
| 22 | 27.280 | 0.400 | 3.2663 | 2364 | 43 |
| 23 | 27.760 | 0.306 | 3.2109 | 1996 | 36 |
| 24 | 30.300 | 0.329 | 2.9473 | 2574 | 47 |
| 25 | 30.880 | 0.118 | 2.8932 | 944 | 17 |
| 26 | 31.140 | 0.118 | 2.8696 | 921 | 17 |
| 27 | 31.840 | 0.141 | 2.8081 | 985 | 18 |
| 28 | 32.000 | 0.165 | 2.7945 | 1003 | 18 |
| 29 | 32.180 | 0.118 | 2.7792 | 822 | 15 |
| 30 | 36.760 | 0.212 | 2.4428 | 871 | 16 |
| 31 | 37.120 | 0.118 | 2.4199 | 1095 | 20 |
| 32 | 37.420 | 0.306 | 2.4012 | 1360 | 25 |
| 33 | 38.380 | 0.141 | 2.3433 | 860 | 16 |
| 34 | 38.560 | 0.259 | 2.3328 | 890 | 16 |

According to the present invention, there is provided crystalline duloxetine free base, Form C, having an X-ray diffraction pattern, or substantially the same X-ray diffraction pattern, as shown in FIG. 3. More particularly, crystalline duloxetine free base Form C according to the present invention can be characterised as having an X-ray diffraction pattern with characteristic peaks (2θ): 12.23, 13.49, 16.90, 18.28, 20.37, 22.61, 27.22, 27.40 and 30.65°.

Further characterising data for crystalline duloxetine free base Form C according to the present invention as obtained by X-ray diffraction is shown in following table 3.

TABLE 3

| Peak No. | 2θ (deg) | FWHM (deg) | d (A) | Intensity (Counts) | I/I₀ |
|---|---|---|---|---|---|
| 1 | 11.160 | 0.306 | 7.9215 | 1911 | 51 |
| 2 | 12.230 | 0.318 | 7.2308 | 919 | 25 |
| 3 | 12.570 | 0.224 | 7.0360 | 872 | 23 |
| 4 | 13.490 | 0.400 | 6.5581 | 1419 | 38 |
| 5 | 15.050 | 0.341 | 5.8817 | 640 | 17 |
| 6 | 16.900 | 0.282 | 5.2417 | 850 | 23 |
| 7 | 18.280 | 0.400 | 4.8490 | 1717 | 46 |
| 8 | 18.840 | 0.388 | 4.7061 | 1646 | 44 |
| 9 | 19.500 | 0.106 | 4.5483 | 941 | 25 |
| 10 | 19.660 | 0.129 | 4.5117 | 1141 | 30 |
| 11 | 20.370 | 0.424 | 4.3560 | 3573 | 94 |
| 12 | 20.810 | 0.271 | 4.2649 | 1890 | 50 |
| 13 | 21.710 | 0.106 | 4.0900 | 637 | 17 |
| 14 | 22.610 | 0.424 | 3.9292 | 3808 | 100 |
| 15 | 23.080 | 0.212 | 3.8503 | 1206 | 32 |
| 16 | 23.850 | 0.247 | 3.7277 | 725 | 20 |
| 17 | 25.140 | 0.318 | 3.5393 | 958 | 26 |
| 18 | 25.570 | 0.318 | 3.4807 | 1065 | 28 |
| 19 | 27.220 | 0.141 | 3.2733 | 1534 | 41 |
| 20 | 27.400 | 0.400 | 3.2522 | 1778 | 47 |
| 21 | 27.830 | 0.129 | 3.2030 | 786 | 21 |
| 22 | 28.030 | 0.129 | 3.1806 | 704 | 19 |
| 23 | 28.440 | 0.224 | 3.1356 | 696 | 19 |
| 24 | 29.730 | 0.153 | 3.0024 | 696 | 19 |
| 25 | 30.180 | 0.129 | 2.9587 | 989 | 26 |
| 26 | 30.650 | 0.471 | 2.9144 | 1636 | 43 |
| 27 | 32.340 | 0.129 | 2.7658 | 746 | 20 |
| 28 | 32.530 | 0.224 | 2.7501 | 836 | 22 |
| 29 | 34.420 | 0.200 | 2.6033 | 708 | 19 |
| 30 | 34.900 | 0.118 | 2.5686 | 760 | 20 |
| 31 | 35.080 | 0.188 | 2.5558 | 787 | 21 |
| 32 | 36.730 | 0.235 | 2.4447 | 815 | 22 |
| 33 | 36.990 | 0.106 | 2.4281 | 785 | 21 |
| 34 | 37.230 | 0.271 | 2.4130 | 812 | 22 |
| 35 | 40.430 | 0.106 | 2.2291 | 796 | 21 |
| 36 | 40.600 | 0.176 | 2.2202 | 813 | 22 |
| 37 | 42.970 | 0.306 | 2.1030 | 1057 | 28 |

There is also provided by the present invention a pharmaceutically acceptable salt of duloxetine, which pharmaceutically acceptable salt is prepared from duloxetine free base in crystalline form as provided by the present invention. Preferred pharmaceutically acceptable salts of duloxetine as provided by the present invention include duloxetine hydrochloride and duloxetine oxalate, especially duloxetine hydrochloride.

A pharmaceutically acceptable salt of duloxetine as provided by the present invention is preferably at least about 99.5% w/w pure.

Crystalline duloxetine free base as provided by the present invention can in turn be prepared from salts of duloxetine, such as the oxalate salt, hydrochloride salt, di-p-toluyl tartarate salt, or any other suitable salt. According to the present invention, there is further provided a process of preparing crystalline duloxetine free base, which process comprises dissolving or suspending a salt of duloxetine in a suitable medium, such as water, neutralizing with a suitable base, such as an alkali metal hydroxide, typically sodium hydroxide, extracting the thus formed duloxetine free base into a suitable solvent, replacing the solvent with a non-solvent, and thus isolating duloxetine free base in crystalline form.

It is also possible to interconvert distinct polymorphic forms of crystalline duloxetine free base as provided by the present invention. There is, therefore, further provided by the present invention an interconversion process, whereby a second polymorphic form of crystalline duloxetine free base is prepared from a distinct first polymorphic form of crystalline duloxetine free base. Suitably, the first polymorphic form of crystalline duloxetine free base which is employed as the starting material is dissolved or suspended in a suitable lower alcohol solvent, preferably methanol, and the second polymorphic form is re-crystallized therefrom. Preferably, this interconversion process is employed for the preparation of crystalline duloxetine free base Form B from Form A substantially as hereinafter described in further detail.

The preparation of crystalline duloxetine free base according to the present invention is advantageous in that crystalline duloxetine free base can be employed as a useful intermediate in the preparation of highly pure pharmaceutically acceptable salts of duloxetine, in particular duloxetine oxalate or hydrochloride. Pharmaceutically acceptable salts of duloxetine prepared from crystalline duloxetine free base can exhibit beneficial properties, for example, duloxetine hydrochloride prepared from crystalline duloxetine free base as provided by the present invention is more resistant to degradation than duloxetine hydrochloride prepared by conventional methods known from the prior art.

According to the present invention there is further provided a process of preparing crystalline duloxetine free base Form A, which process comprises suspending or dissolving a duloxetine salt, such as the hydrochloride or di-p-toluyl tartarate salt of duloxetine, in water, neutralizing with a base, such as an alkali metal hydroxide, typically sodium hydroxide, extracting into a substantially water immiscible solvent, such as dichloromethane, concentrating the substantially water immiscible solvent, replacing the substantially water immiscible solvent with acetone and thus isolating duloxetine free base Form A in crystalline form. Crystalline duloxetine free base Form A is characterized by powder x-ray diffraction substantially as shown in FIG. 1.

According to the present invention there is further provided a process of preparing crystalline duloxetine free base Form B, which process comprises dissolving or suspending a first polymorphic form of crystalline duloxetine free base, typically duloxetine free base Form A, in a suitable lower alcohol solvent, preferably methanol, and recrystallizing duloxetine free base Form B therefrom. Crystalline duloxetine free base Form B is characterized by powder x-ray diffraction substantially as shown in FIG. 2.

According to the present invention there is further provided a process of preparing crystalline duloxetine free base Form C, which process comprises suspending or dissolving a duloxetine salt, such as the hydrochloride or di-p-toluyl tartarate salt of duloxetine, in water, neutralizing with a base, such as an alkali metal hydroxide, typically sodium hydroxide, extracting into a substantially water immiscible solvent, such as dichloromethane, concentrating the substantially water immiscible solvent, replacing the substantially water immiscible solvent with isopropanol and thus isolating duloxetine free base Form C in crystalline form. Crystalline duloxetine free base Form C is characterized by powder x-ray diffraction substantially as shown in FIG. 3.

There is also provided by the present invention a process of preparing a pharmaceutically acceptable salt of duloxetine, which process comprises dissolving or suspending crystalline duloxetine free base as provided by the present invention in a water miscible solvent, such as acetone, adding a pharmaceutically acceptable acid thereto required to form the pharmaceutically acceptable salt, and isolating the required pharmaceutically acceptable salt of duloxetine in crystalline form. Any of polymorphic forms A, B or C of crystalline duloxetine free base as provided by the present invention can be employed as crystalline duloxetine free base starting material for the above process of preparing a pharmaceutically acceptable salt of duloxetine.

Suitable acid addition salts which can be prepared from crystalline duloxetine free base according to the present invention include those formed with pharmaceutically acceptable organic or inorganic acids and are well known to those of skill in the art. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, ∃-hydroxybutyrate, glycollate, maleate, tartrate, methanesulfonate, propanesulfonates, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and those formed with organic acids such as oxalic acid and maleic acid. A particularly preferred acid addition salt is the hydrochloride.

As noted above, duloxetine is a dual serotonin and norepinephrine reuptake inhibitor. The present invention further provides a pharmaceutically acceptable formulation for administering to a patient, including humans, suffering from, or susceptible to, a disease state prevented, ameliorated or eliminated by the administration of a serotonin and/or norepinephrine reuptake inhibitor, which formulation comprises a therapeutically effective amount of crystalline duloxetine free base, optionally as any of Forms A, B or C, substantially as hereinbefore described, or a pharmaceutically acceptable salt of duloxetine as provided by the present invention substantially as hereinbefore described, together with a pharmaceutically acceptable carrier, diluent or excipient therefor.

As used herein, the term "therapeutically effective amount" means an amount of crystalline duloxetine free base, optionally as any of Forms A, B or C, substantially as hereinbefore described, or a pharmaceutically acceptable salt of duloxetine as provided by the present invention substantially as hereinbefore described, which is capable of preventing, ameliorating or eliminating a disease state for which administration of a serotonin and/or norepinephrine reuptake inhibitor is indicated.

By "pharmaceutically acceptable formulation" it is meant that the carrier, diluent or excipient is compatible with crystalline duloxetine free base, optionally as any of Forms A, B or C, substantially as hereinbefore described, or a pharmaceutically acceptable salt of duloxetine as provided by the present invention substantially as hereinbefore described, and not deleterious to a recipient thereof.

Pharmaceutical formulations as provided by the present invention can be prepared by known procedures using well known and readily available ingredients. In preparation of formulations as provided by the present invention, crystalline duloxetine free base, optionally as any of Forms A, B or C, substantially as hereinbefore described, or a pharmaceutically acceptable salt of duloxetine as provided by the present invention substantially as hereinbefore described, can be mixed with a carrier, diluent or excipient therefor. Formulations as provided by the present invention can be in the form of tablets, pills, powders, lozenges, sachets, cachets, elixirs, suspensions, emulsions, solutions, syrups, aerosol, ointments containing, for example, up to 10% by weight of crystalline duloxetine free base, optionally as any of Forms A, B or C, substantially as hereinbefore described, or a pharmaceutically acceptable salt of duloxetine as provided by the present invention substantially as hereinbefore described, soft and hard gelatin capsules, suppositories, sterile injectable solutions and sterile packaged powders. In particular, capsules are suitable formulations for use in accordance with the present invention, which can typically include coated non pareil seeds substantially as hereinafter illustrated in further detail by reference to the Examples.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The formulations of the invention may be formulated so as to provide quick, sustained or delayed release of crystalline duloxetine free base, optionally as any of Forms A, B or C, substantially as hereinbefore described, or a pharmaceutically acceptable salt of duloxetine as provided by the present invention substantially as hereinbefore described, after administration to the patient by employing procedures well known in the art.

The formulations are preferably formulated in a unit dosage form, each dosage containing from about 5 to about 500 mg, more usually about 25 to about 300 mg, of crystalline duloxetine free base, optionally as any of Forms A, B or C, substantially as hereinbefore described, or a pharmaceutically acceptable salt of duloxetine as provided by the present invention substantially as hereinbefore described. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

There is also provided by the present invention crystalline duloxetine free base, optionally as any of Forms A, B or C, substantially as hereinbefore described, or a pharmaceutically acceptable salt of duloxetine as provided by the present invention substantially as hereinbefore described, for use in therapy.

The present invention further provides crystalline duloxetine free base, optionally as any of Forms A, B or C, substantially as hereinbefore described, or a pharmaceutically acceptable salt of duloxetine as provided by the present invention substantially as hereinbefore described, for use in the manufacture of a medicament for the treatment of a disease state prevented, ameliorated or eliminated by the administration of a serotonin and/or norepinephrine reuptake inhibitor as described herein.

The present invention also provides a method of treating a disease state prevented, ameliorated or eliminated by the administration of a serotonin and/or norepinephrine reuptake inhibitor in a patient in need of such treatment, which method comprises administering to the patient a therapeutically effective amount of crystalline duloxetine free base, optionally as any of Forms A, B or C, substantially as hereinbefore described, or a pharmaceutically acceptable salt of duloxetine as provided by the present invention substantially as hereinbefore described.

A variety of physiologic functions have been shown to be subject to influence by brain serotoninengic and norepinephrinergic neural systems. As such, crystalline duloxetine free base, optionally as any of Forms A, B or C, substantially as hereinbefore described, of the present invention, or a pharmaceutically acceptable salt of duloxetine as provided by the present invention substantially as hereinbefore described, has utility in the treatment of a variety of disorders in mammals associated with these neural systems such as obesity, depression, alcoholism, pain, loss of memory, anxiety and smoking. In particular, crystalline duloxetine free base, optionally as any of Forms A, B or C, substantially as hereinbefore described, or a pharmaceutically acceptable salt of duloxetine as provided by the present invention substantially as hereinbefore described, has utility in the treatment of depression.

In a preferred aspect of the present invention, therefore, there is provided crystalline duloxetine free base, optionally as any of Forms A, B or C, substantially as hereinbefore described, or a pharmaceutically acceptable salt of duloxetine as provided by the present invention substantially as hereinbefore described, for use in the manufacture of a medicament for the treatment of depression.

In a preferred aspect of the present invention, therefore, there is also provided a method of treating depression in a patient in need of such treatment, which method comprises administering to the patient a therapeutically effective amount of crystalline duloxetine free base, optionally as any of Forms A, B or C, substantially as hereinbefore described, or a pharmaceutically acceptable salt of duloxetine as provided by the present invention substantially as hereinbefore described.

The particular dose of crystalline duloxetine free base, optionally as any of Forms A, B or C, substantially as hereinbefore described, or a pharmaceutically acceptable salt of duloxetine as provided by the present invention substantially as hereinbefore described, administered according to this invention will of course be determined by the particular circumstances surrounding the case, the route of administration, the particular condition being treated, and similar considerations. Crystalline duloxetine free base, optionally as any of Forms A, B or C, substantially as hereinbefore described, or a pharmaceutically acceptable salt of duloxetine as provided by the present invention substantially as hereinbefore described, can be administered by a variety of routes including the oral, rectal, transdermal, subcutaneous, intravenous, intramuscular or intranasal routes. A typical daily dose will contain from about 0.01 mg/kg to about 20 mg/kg of crystalline duloxetine free base, optionally as any of Forms A, B or C, substantially as hereinbefore described, of the present invention, or a pharmaceutically acceptable salt of duloxetine as provided by the present invention substantially as hereinbefore described. Preferred daily doses will be about 0.05 to about 10 mg/kg, ideally about 0.1 to about 5 mg/kg.

BRIEF DESCRIPTION OF THE DRAWINGS

The present invention will now be further illustrated by the Figures and following Examples, which do not limit the scope of the invention in any way.

Figure 1:
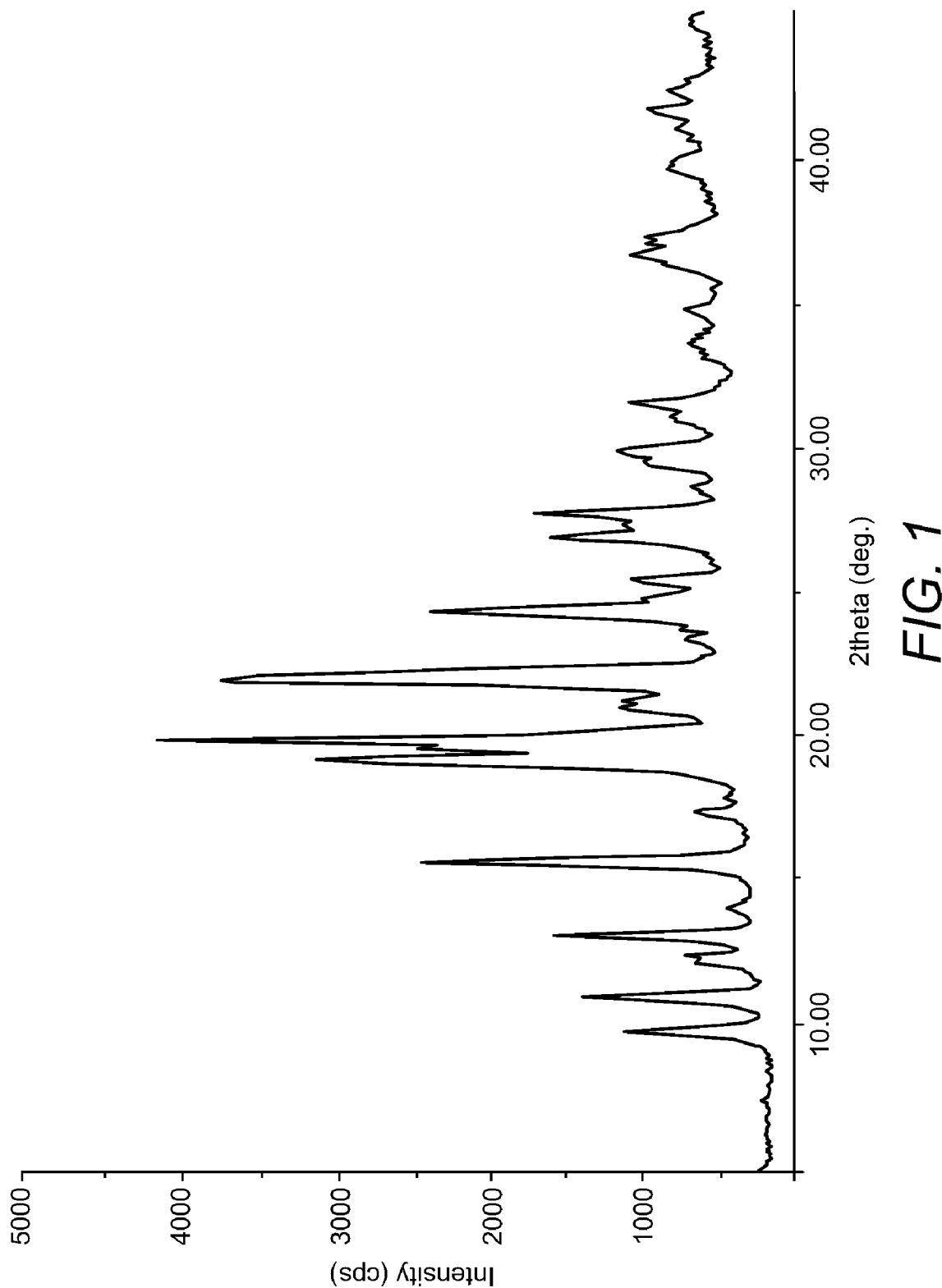
FIG. 1 is a powder X-ray diffraction pattern for crystalline duloxetine free base Form A.
Figure 2:
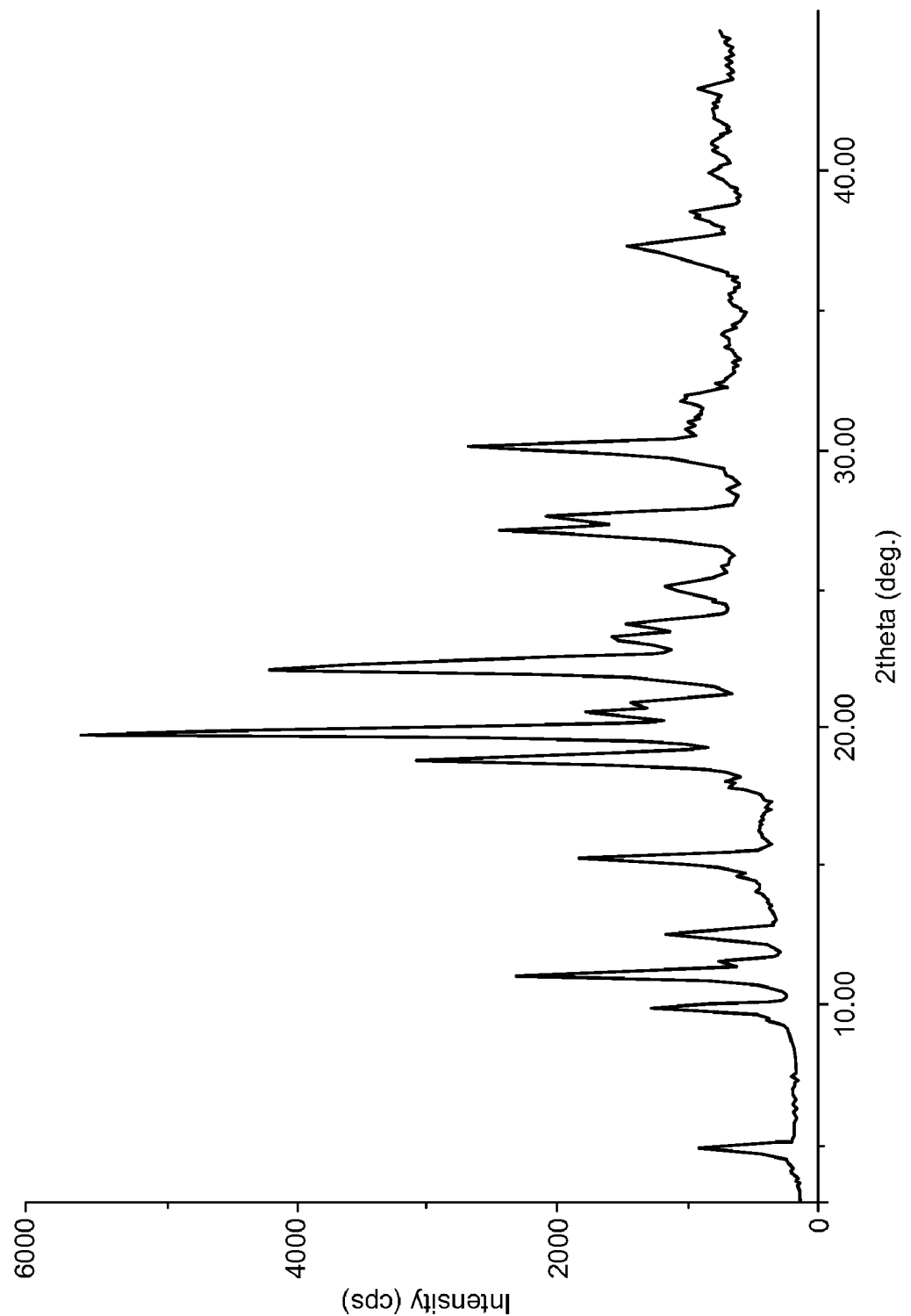
FIG. 2 is a powder X-ray diffraction pattern for crystalline duloxetine free base Form B.
Figure 3:
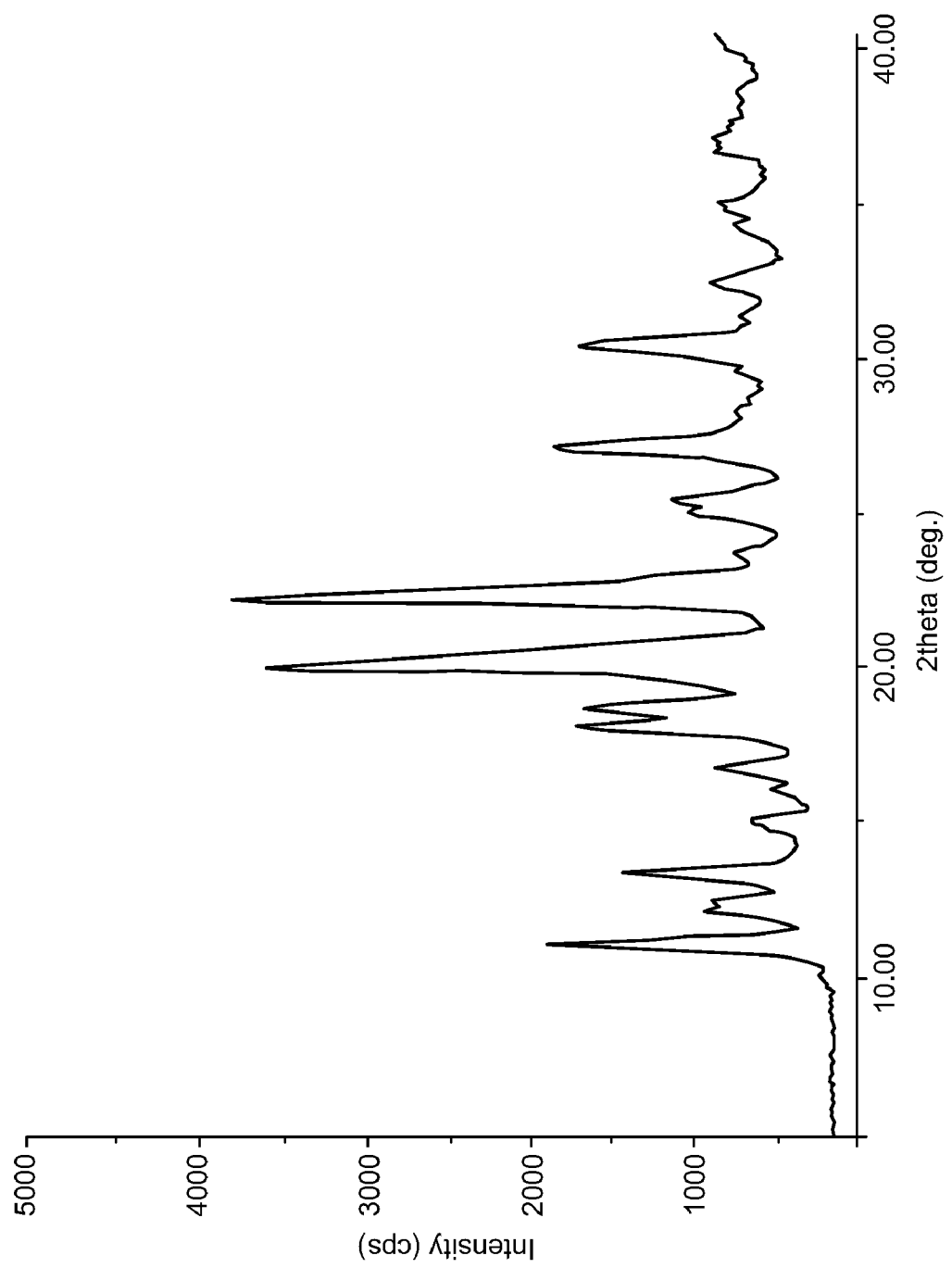
FIG. 3 is a powder X-ray diffraction pattern for crystalline duloxetine free base Form C.

The above referred to X-ray diffraction patterns were obtained on a Rigaku Miniflex X-ray Diffractometer equipped with a Cu Kα source and a scintillation counter detector. The scan speed was 2 degrees per minute and the range was from 3 to 45 degrees.

EXAMPLES

Reference Example

Preparation of Duloxetine (−)di-p-toluyl Tartarate

1. Racemic Duloxetine (100 gm) was added to methanol (200 ml).
2. (−) Di-p-Toluoyl-L-Tartaric acid (130 gm) was added lot wise at 25-30° C.
3. The contents were heated to 60-65° C. and maintained for 1 hour at 60-65° C.
4. Methanol was completely distilled under vacuum at 45-50° C.

5. Acetone (1.5 lit) was added to the residue and stirred for 3 hours at 25-30° C.
6. The solids were filtered, washed with acetone (100 ml) and dried under vacuum at 45-50° C. to give the title compound (80 gm).

Example 1

Preparation of Duloxetine Free Base (Form A)

1. To Duloxetine (−) Di-p-toluyl tartarate (100 gm), prepared by the above Reference Example, was charged water (1 lit), followed by stirring at 25-30° C. for 15 minutes.
2. Slowly, lye solution (8 gm sodium hydroxide in 50 ml water) was added and stirred for 10-15 minutes at 25-30° C.
3. The mixture was extracted twice with methylene chloride (500 ml).
4. Combined methylene chloride layers were washed with water (100 ml).
5. Methylene chloride was distilled out under vacuum at a temperature less than 40° C., and stripped off with acetone (50 ml).
6. The residue was stirred with acetone (1 lit) at room temperature for 1 hour.
7. The solids were filtered and dried under vacuum at 50-55° C. to obtain duloxetine base Form A (25 gm).

Example 2

Preparation of Duloxetine Free Base (Form B)

1. Duloxetine free base Form A (10 g) was dissolved in methanol (250 ml) at 55-60° C.
2. The solution was cooled to room temperature.
3. The solution was stirred at room temperature for 1 hour.
4. The solids were filtered and washed with methanol (10 ml).
5. The solids were dried under vacuum at 50-55° C. to give duloxetine free base Form B (7 gm).

Example 3

Preparation of Duloxetine Free Base (Form C)

1. To Duloxetine (−) Di-p-toluyl tartarate (100 gm), prepared by the above Reference Example, was charged water (1 lit), followed by stirring at 25-30° C. for 15 minutes.
2. Slowly, lye solution (8 gm sodium hydroxide in 50 ml water) was added and stirred for 10-15 minutes at 25-30° C.
3. The mixture was extracted twice with methylene chloride (500 ml).
4. Combined methylene chloride layers were washed with water (100 ml).
5. Methylene chloride was distilled out under vacuum at a temperature less than 40° C., and stripped off with isopropanol (50 ml).
6. The residue was stirred with isopropanol (500 ml) at room temperature for 1 hour.
7. The solids were filtered and dried under vacuum at 50-55° C. to obtain duloxetine free base Form C (25 gm).

Example 4

Preparation of Duloxetine Hydrochloride

1. Duloxetine free base Form A (25 gm) and acetone (250 ml) were stirred for 15 minutes at 25-30° C.
2. The pH of the mixture was adjusted to 2.0-3.0 using 20% isopropanolic HCl at 25-30° C.
3. The solids were filtered, washed with acetone (100 ml) and dried under vacuum at 50-55° C. to give duloxetine hydrochloride (25 gm).

Example 5

Preparation of Duloxetine Hydrochloride

In a manner analogous to Example 4, duloxetine free base Form B was converted to duloxetine hydrochloride.

Example 6

Duloxetine Capsules (Duloxetine Base According to the Present Invention)—60 Mg

| Sr. No | Ingredients | Qty (mg/capsule) |
|---|---|---|
| I. | Drug Loading | |
| 1. | Duloxetine | 60 mg |
| 2. | Non pareil seeds | 110-140 mg |
| 3. | Hydroxy propyl methyl cellulose | 2.0-4.0 |
| 4. | Talc | 1.5-2.8 |
| 5. | Colloidal Silicon Dioxide | 0.5-1.5 |
| 6. | Isopropyl Alcohol | q.s |
| 7. | Methylene chloride | q.s |
| II. | Seal Coating | |
| 1. | Hydroxy propyl methyl cellulose | 7-10 |
| 2. | Propylene Glycol | 2-4 |
| 3. | Talc | 2-4 |
| 4. | Isopropyl Alcohol | q.s |
| 5. | Methylene chloride | q.s |
| III. | Eudragit Coating | |
| 1. | Eudragit L 100-55 | 10-20 |
| 2. | Talc | 4-8 |
| 3. | Titanium dioxide | 2-5 |
| 4. | Triethyl citrate | 1.5-3.0 |
| 5. | Sodium hydroxide | 0.1-0.5 |
| 6. | Purified water | q.s |

Manufacturing process—Drug loading in glatt GPCG 1.1 by bottom spray.

Example 7

Duloxetine Capsules (Duloxetine Base According to the Present Invention)—60 Mg

| Sr. No | Ingredients | Qty (mg/capsule) |
|---|---|---|
| I. | Drug Loading | |
| 1. | Duloxetine | 60 mg |
| 2. | Non pareil seeds | 110-140 |
| 3. | Hydroxy propyl methyl cellulose | 2.0-4.0 |
| 4. | Talc | 1.5-2.5 |
| 5. | Colloidal Silicon Dioxide | 0.5-1.5 |
| 6. | Mannitol | 60 mg |
| II. | Seal Coating | |
| 1. | Hydroxy propyl methyl cellulose | 7-10 |
| 2. | Mannitol | 3.0-9.0 |
| 3. | Talc | 3.5-4.5 |
| 4. | Propylene Glycol | 1.5-2.5 |
| 5. | Purified water | q.s |
| III. | Eudragit Coating | |
| 1. | Budragit | 9-11 |
| 2. | Talc | 2.0-4.0 |
| 3. | Titanium dioxide | 1.0-3.0 |
| 4. | Tiethyl citrate | 1.0-3.0 |
| 5. | Sodium hydroxide | 0.1-0.3 |
| 6. | Purified water | q.s |

Manufacturing process—Drug loading in rotar coater.

Example 8

Duloxetine Hydrochloride Capsules (Duloxetine Hydrochloride as Provided According to the Present Invention)—60 mg

| Sr. No | Ingredients | Qty (mg/capsule) |
|---|---|---|
| I. | Drug Loading | |
| 1. | Duloxetine Hydrochloride | 60 mg |
| 2. | Non pareil seeds | 110-140 mg |
| 3. | Hydroxy propyl methyl cellulose | 2.0-4.0 |
| 4. | Talc | 1.5-2.8 |
| 5. | Colloidal Silicon Dioxide | 0.5-1.5 |
| 6. | Isopropyl Alcohol | q.s |
| 7. | Methylene chloride | q.s |
| II. | Seal Coating | |
| 1. | Hydroxy propyl methyl cellulose | 7-10 |
| 2. | Propylene Glycol | 2-4 |
| 3. | Talc | 2-4 |
| 4. | Isopropyl Alcohol | q.s |
| 5. | Methylene chloride | q.s |
| III. | Eudragit Coating | |
| 1. | Eudragit L 100-55 | 10-20 |
| 2. | Talc | 4-8 |
| 3. | Titanium dioxide | 2-5 |
| 4. | Tiethyl citrate | 1.5-3.0 |
| 5. | Sodium hydroxide | 0.1-0.5 |
| 6. | Purified water | q.s |

Manufacturing process—Drug loading in glatt GPCG 1.1 by bottom spray.

Example 9

Duloxetine Hydrochloride Capsules (Duloxetine Hydrochloride as Provided According to the Present Invention)—60 mg

| Sr. No | Ingredients | Qty (mg/capsule) |
|---|---|---|
| I. | Drug Loading | |
| 1. | Duloxetine Hydrochloride | 60 mg |
| 2. | Non pareil seeds | 110-140 |
| 3. | Hydroxy propyl methyl cellulose | 2.0-4.0 |
| 4. | Talc | 1.5-2.5 |
| 5. | Colloidal Silicon Dioxide | 0.5-1.5 |
| 6. | Mannitol | 60 mg |
| II. | Seal Coating | |
| 1. | Hydroxy propyl methyl cellulose | 7-10 |
| 2. | Mannitol | 3.0-9.0 |
| 3. | Talc | 3.5-4.5 |
| 4. | Propylene Glycol | 1.5-2.5 |
| 5. | Purified water | q.s |
| III. | Eudragit Coating | |
| 1. | Eudragit | 9-11 |
| 2. | Talc | 2.0-4.0 |
| 3. | Titanium dioxide | 1.0-3.0 |
| 4. | Tiethyl citrate | 1.0-3.0 |
| 5. | Sodium hydroxide | 0.1-0.3 |
| 6. | Purified water | q.s |

Manufacturing process—Drug loading in rotar coater.

Example 10

Forced degradation study on duloxetine hydrochloride produced according to the prior art (Preparation 2, U.S. Pat. No. 5,491,243) and duloxetine hydrochloride produced from crystalline duloxetine free base according to the present invention:

|  | DULOXETINE HCl (from prior art) | | | DULOXETINE HCl (from free base) | | |
| --- | --- | --- | --- | --- | --- | --- |
| STRESS CONDITION | Description | SMI | Total imp | Description | SMI | Total imp |
| 1. Heat/UV | | | | | | |
| a) Before exposure to heat or light | White powder | 0.20% | 0.48% | White powder | 0.05% | 0.11% |
| b) 45° C. | Cream coloured powder | 0.19% | 0.65% | White powder | 0.07% | 0.12% |
| c) 60° C. | Light pink coloured powder | 0.19% | 0.70% | White powder | 0.07% | 0.12% |
| d) UV | Light brown coloured powder | 0.19% | 0.66% | Cream coloured powder | 0.06% | 0.11% |

"SMI" - Single maximum impurity

The invention claimed is:

1. Duloxetine free base in crystalline form having Form A and characterized as having an X-ray diffraction pattern with characteristic peaks (2θ): 15.61, 19.19, 19.88, and 21.94°.

2. The crystalline duloxetine free base of claim 1, characterized as having an X-ray diffraction pattern with additional characteristic peaks (2θ): 9.70, 10.88, 13.03, 19.55, 22.16, 26.95 and 27.76°.

3. Duloxetine free base in crystalline form having Form B and characterized as having an X-ray diffraction pattern with characteristic peaks (2θ): 4.98, 15.32, 22.32, 22.44, and 30.30°.

4. The crystalline duloxetine free base of claim 3, characterized as having an X-ray diffraction pattern with additional characteristic peaks (2θ): 9.96, 11.18, 12.58, 18.98, 20.04, 20.62, and 27.28°.

5. Duloxetine free base in crystalline form having Form C and characterized as having an X-ray diffraction pattern with characteristic peaks (2θ): 18.28, 22.61, 27.40, and 30.65°.

6. The crystalline duloxetine free base of claim 5, characterized as having an X-ray diffraction pattern with additional characteristic peaks (2θ): 12.23, 13.49, 16.90, 20.37, and 27.22°.

* * * * *

UNITED STATES PATENT AND TRADEMARK OFFICE
CERTIFICATE OF CORRECTION

| | | |
|---|---|---|
| PATENT NO. | : 7,951,837 B2 | Page 1 of 1 |
| APPLICATION NO. | : 11/568784 | |
| DATED | : May 31, 2011 | |
| INVENTOR(S) | : Rajendra Narayanrao Kankan et al. | |

It is certified that error appears in the above-identified patent and that said Letters Patent is hereby corrected as shown below:

On the title page of the patent, Item (75), Inventors, replace "Revikumar Puppala" with
-- Ravikumar Puppala --

Signed and Sealed this
Nineteenth Day of July, 2011

David J. Kappos
*Director of the United States Patent and Trademark Office*